United States Patent

Fujiura et al.

[11] Patent Number: 5,904,028
[45] Date of Patent: May 18, 1999

[54] FRAGRANCE AND DEODORANT MATERIALS

[75] Inventors: Yoji Fujiura, Kyoto; Yukio Zenitani, Nara-ken, both of Japan

[73] Assignee: Sanyo Chemical Industries, Ltd., Kyoto, Japan

[21] Appl. No.: 08/950,367

[22] Filed: Oct. 14, 1997

[30] Foreign Application Priority Data

Oct. 11, 1996 [JP] Japan ................................. 8-289269

[51] Int. Cl.⁶ .............................. B65B 3/04; B65B 61/20
[52] U.S. Cl. .............................. 53/431; 53/428; 53/455; 53/474; 239/56
[58] Field of Search ............................ 53/400, 410, 428, 53/431, 455, 445, 155, 474; 239/56, 55

[56] References Cited

U.S. PATENT DOCUMENTS

| | | | |
|---|---|---|---|
| 3,096,148 | 7/1963 | Walker | 53/428 X |
| 4,094,119 | 6/1978 | Sullivan | 53/400 |
| 4,174,598 | 11/1979 | Shepherd et al. | 53/431 |
| 4,594,835 | 6/1986 | Gray | 53/474 |
| 5,324,490 | 6/1994 | Van Vlahakis et al. | 239/55 |
| 5,765,751 | 6/1998 | Joshi | 239/56 |

FOREIGN PATENT DOCUMENTS

| | | | |
|---|---|---|---|
| 2640858 | 6/1990 | France | 53/400 |
| 7000494 | 1/1995 | Japan . | |

*Primary Examiner*—Linda Johnson
*Attorney, Agent, or Firm*—Roylance, Abrams, Berdo & Goodman, L.L.P.

[57] ABSTRACT

A diffusing device containing a fragrance or deodorant material includes a gel of a water swellable/water absorbing resin carrying the fragrance and/or deodorant components. The fragrance or deodorant release device can be readily produced on an industrial scale, is easy for a user to handle, and employs a water swellable/water absorbing resin. The gel is produced by enclosing a water swellable/water absorbing resin in a water resistant container, such as a packet, having a water permeable portion and immersing the packet into an aqueous medium containing the fragrance and/or deodorant components whereby the resin absorbs the fragrance and/or deodorant components.

28 Claims, 1 Drawing Sheet

FRAGRANCE AND DEODORANT MATERIALS

FIELD OF THE INVENTION

The present invention relates to a sustained fragrance release or deodorant release device employing a water swellable/water absorbing resin having a fragrance or deodorant absorbed in the resin.

DESCRIPTION OF THE RELATED ART

Conventional fragrance or deodorant materials are known to employ a water swellable/water absorbing resin. One type of fragrance or deodorant material includes a water swellable/water absorbing resin impregnated with fragrance or deodorant components. The impregnated resin is then placed in containers made of, for example, plastic and glass. Another type of fragrance or deodorant material places a fragrance and a water absorbing resin in a container. The user forms the resulting composition by mixing the fragrance with the water absorbing resin in the container. An example of this type of material is disclosed in Japanese Kokoku No. 6-38847.

Other fragrance or deodorant products are produced by mixing a dry powdered fragrance and a water absorbing resin powder together and then adding water to form a gel. The resulting gel is then placed in a desired container. An example of this type of product is disclosed in Japanese Kokoku No. 61-47545. These materials employing water swellable/water absorbing resins generally exhibit excellent long-lasting fragrance or deodorant release characteristics. The products are typically used as room fresheners so that the containers are designed to be aesthetically attractive.

However, in the products where the water swellable/water absorbing resin is placed in the container of, for example, plastic and glass, the gel particles may spill from the container when the container turns over sideways.

Furthermore, the gelled water swellable/water absorbing resin particles often coagulate and stick to one another and are not easily handled on an industrial scale in a gelled form. This results in added handling costs when using such gelled resins. In order to prevent these problems, additional handling steps are required, such as, for example, blending the fragrance composition and the water swellable/water absorbing resin, and then adding the water to form the gel.

Furthermore, concerns for the design for the shape of containers for interior-design rather than the fragrant or deodorant characteristics results in increased waste, which is not desirable from an ecological view point.

SUMMARY OF THE INVENTION

The present invention is directed to a diffusing device for the sustained release of a fragrance, deodorant or other volatile material which can be readily mass produced with low cost. Accordingly, an object of the invention is to provide a fragrance release or deodorant device having a simple shape that does not require additional mixing or preparation steps by the consumer prior to use.

Another object of the invention is to provide a diffusing device having extended fragrance release or deodorizing characteristics that is easy to manufacture and which can be readily mass produced at a low cost, which is easy to handle, and exhibits excellent long-lasting fragrance or deodorant release characteristics.

A further aspect of the present invention, is to provide a fragrance or deodorant packet containing a gel formed from a water swellable/water absorbing resin carrying fragrance and/or deodorant components.

Another object of the invention is to provide a gel produced from a water swellable/water absorbing resin and an aqueous medium containing a fragrance and/or deodorant component.

Another object of the invention is to provide a fragrance or deodorant release device containing gelled resin particles where the gelled particles cannot spill from the device.

Another object of the invention is to provide a process where direct handling of the gel is avoided for mass production of a fragrance or deodorant release device.

A still further object of the invention is to provide a fragrance or deodorant release device in the form of a flexible bag-like packet containing a gel of a water swelling/water absorbing resin and a fragrance or deodorant material.

Another object of the invention is to provide a process of producing a fragrance or deodorant release device by enclosing a water swelling/water absorbing resin in a porous container and immersing the container in an aqueous solution of a fragrance or deodorant for sufficient time for the resin to absorb the solution and form a gel.

The objects of the invention are basically attained by providing a device for releasing a volatile component to the atmosphere, wherein said device comprises a gel formed from a water absorbing gel-forming resin and at least one volatile component, and a water insoluble container completely enclosing said gel, wherein said device is produced by the process comprising the steps of enclosing a water absorbing gel-forming resin in a water insoluble container having at least one water permeable portion, and contacting said container with an aqueous medium containing at least one volatile component whereby said aqueous medium penetrates said porous portion and is absorbed by said resin to produce said gel containing said volatile component.

The objects of the invention are further attained by providing a device for the sustained release of at least one volatile component comprising a flexible packet made from a substantially water insoluble material and having at least water permeable portion, and a gelled water absorbing resin containing at least one volatile component, wherein said device is produced by a process comprising the steps of enclosing a substantially dry water absorbing gellable resin in a flexible packet, wherein said packet has a first side formed from a water insoluble and water permeable nonwoven fabric and a second side made from a water insoluble, water impermeable sheet material, contacting said packet with an aqueous medium containing at least one volatile material whereby said aqueous medium penetrates said water permeable layer and is absorbed by said resin to form a gel containing said volatile material.

The objects of the invention are further attained by providing a process of producing a diffusing device for the sustained release of a volatile component, said process comprising the steps of forming a substantially closed container containing a substantially dry water absorbing, gellable resin, wherein said container is substantially water insoluble and includes at least one water permeable portion for enabling water to pass through while retaining said resin in said container, and contacting said container with an aqueous medium containing at least one volatile component whereby said aqueous medium passes through said water permeable portion and contacts said resin to form a gelled resin containing said at least one volatile component.

These and other objects, advantages and salient features of the invention will become apparent from the following detailed description, which, taken in conjunction with the annexed drawings, discloses preferred embodiments of the invention.

BRIEF DESCRIPTION OF THE DRAWINGS

Referring to the drawings which form a part of this original disclosure, in which.

DETAILED DESCRIPTION OF THE INVENTION

Figure 1:
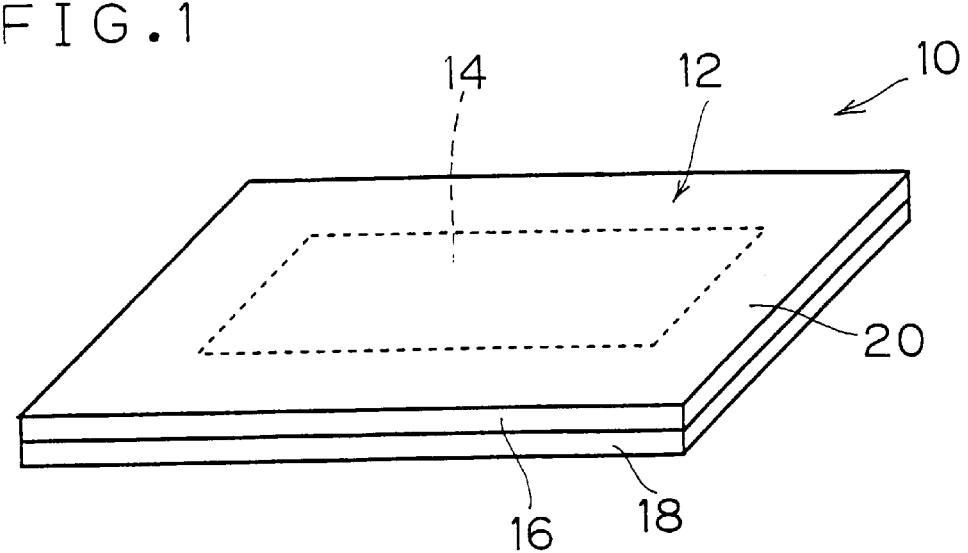
FIG. 1 is a perspective view showing an embodiment of a device of the invention containing a water swellable/water absorbing resin.

The present invention is directed to a diffusing device for the sustained release of components and to a process for producing the diffusing and sustained release device. More particularly, the invention is directed to a device for the sustained release of a volatile compound to the atmosphere. In preferred embodiments of the invention, the volatile compound is a fragrance, odor masking compound or deodorant compound. The volatile compound is absorbed in a gel formed from a water absorbing resin which is enclosed in a container such as a flexible packet. Referring to the drawings, the sustained release device 10 in a first embodiment of the invention includes a packet 12 and a gel 14 of a water absorbing resin.

Figure 2:
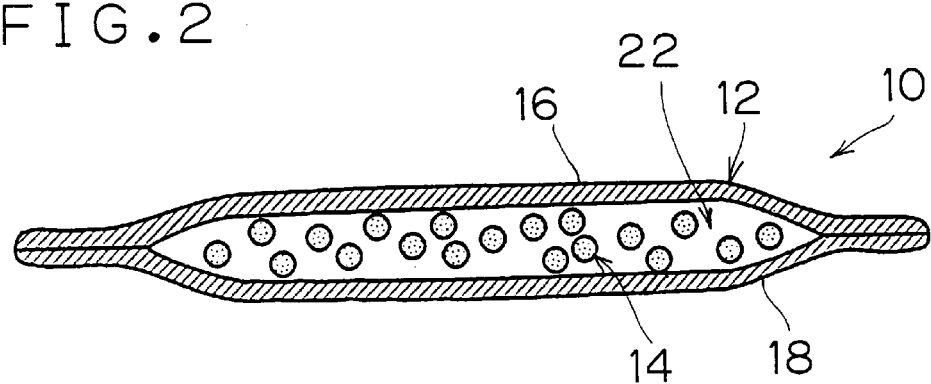
FIG. 2 is a cross sectional view showing an embodiment of a device containing a gelled resin and fragrance or deodorant material in accordance with the present invention.

As shown in FIGS. 1 and 2, packet 12 includes a top sheet portion 16 forming a first layer and bottom sheet portion 18 forming a second layer secured together about their peripheral edges 20 to define hollow cavity 22. The top sheet 16 and bottom sheet 18 are secured together by heat sealing or other known processes to form a continuous seal and prevent the gel 14 from spilling from the packet 12 as discussed hereinafter in greater detail.

Top sheet 16 is a sheet material of water insoluble material and includes at least one water permeable portion. In preferred embodiments top layer 16 is a water permeable non-woven fabric so that the entire top layer 16 of packet 12 is water permeable. Top layer 16 is sufficiently permeable to allow the release of the volatile component but does not permit gel 14 to pass through. In further embodiments, only a portion of the top sheet is permeable.

Top sheet 16 can be made from a number of suitable synthetic and natural materials. Suitable materials include, for example, synthetic polyesters, polyamides and acrylics, semi-synthetic materials of acetate and rayon, natural fibers of cotton, silk and wool and blends or mixtures thereof. The material can be a woven fabric although non-woven fabrics are generally preferred. Non-woven fabrics are generally easier to manufacture into the packet and provide a soft and smooth surface. In further embodiments, top sheet 16 can be a film material having a plurality of fine perforations or a mesh-like opening in the material. Suitable film materials include, for example, polyethylene and polypropylene films.

Top sheet 16 is preferably a towel-like material having a sufficient wet strength for packet 12 to retain its structural integrity when wet. In addition, top sheet 16 must have sufficient strength before and after wetting to resist tearing and spilling of the gel.

Bottom sheet 18 is preferably a non-porous sheet material that is substantially water impermeable. In further embodiments, bottom layer 18 is a porous, water permeable material similar to top sheet 16. In preferred embodiments, bottom sheet 18 is a water impermeable film of a heat sealable material such as, for example, polyethylene or polypropylene. In further embodiments, bottom sheet 18 can be a non-heat sealable material of synthetic resins or metal films, such as, for example, aluminum foil. Packet 12 is preferably formed with bottom layer 18 being a water impermeable material.

Packet 12 as shown in FIG. 1 has a generally rectangular shape although other shapes can be readily used. The function and effectiveness of packet 12 is generally not dependent on the shape of packet 12. Packet 12 is preferably dimensioned for easy handling by the consumer. It has been found that packet 12 having a length of about 10 cm or less results in a product that is convenient and easy to use by the consumer.

In further embodiments, top sheet 16 and bottom sheet 18 are continuous sheets sealed together along the longitudinal edges and along spaced apart transverse lines to form a plurality of packets attached together in the form of a continuous strip. Perforations or frangible lines can be provided between adjacent packets to separate the packets from the strip.

Packet 12 can be produced by a number of processes as known in the art. Preferably, at least one of top layer 16 and the bottom layer 18 is a thermoplastic material capable of forming a heat seal with the other layer. Polyethylene is particularly suitable for providing heat sealing properties to the packet. The edges 20 of packet 12 are preferably heat sealed around the entire perimeter to enclose the gel 14 completely. In embodiments of the invention, both of the top and bottom layers can be made of a heat sealable material so that the layer can be easily bonded together.

In alternative embodiments, where neither the top nor bottom layers are heat sealable, a suitable adhesive can be used to bond the edges together and enclose the gel. The adhesive can be a commercially available water insoluble adhesive as known in the art. Examples of suitable adhesives include hot melt glues and aliphatic resin glues. In other embodiments, a strip of a thermoplastic film can be positioned around the peripheral edges of the top and bottom layers forming a generally unshaped member as viewed in cross-section. Heat and pressure then can be applied along the sides and edges of the thermoplastic film thus adhering the thermoplastic film to the bond the top and bottom layers clamping them together. Alternatively, the edges of the top and bottom layers could be sewn together. However, heat sealing is the preferred method of bonding layers since this method is cost effective and efficient for commercial production.

Although in the preferred embodiments the container is a flexible packet as shown in FIGS. 1 and 2, the container can have any desired shape or dimension. The container can be, for example, a rigid box-like or spherical structure.

The diffusing device 10 is produced by placing a gellable, water absorbing resin in a container, such as packet, and contacting the packet with an aqueous medium containing a volatile component. The aqueous medium penetrates the porous, water permeable portion of the packet and contacts the resin whereby the resin absorbs the aqueous medium and swells to form a gelled resin containing the volatile component as shown in FIG. 2. The aqueous medium can be an aqueous solution, an aqueous emulsion or aqueous dispersion. The aqueous medium contains an effective amount of a volatile component, such as a fragrance, odor masking agent or deodorant to provide sustained release of the component over a selected period of time. The concentration of the volatile component in the aqueous medium depends on the particular component and the desired sustained release properties. The aqueous medium generally contains about 1% by weight of the volatile component although the amount can range from about 0.1% to about 30.0% by weight based on the total weight of the aqueous medium.

Examples of the water swellable/water absorbing resin for use in the present invention include water absorbing resins prepared by polymerizing a composition comprising starch or cellulose; a water soluble monomer containing hydrophilic groups such as, carboxyl groups and sulfonic groups, and/or a monomer than can be converted to a water soluble group by subsequent hydrolysis; and a crosslinking agent, followed by hydrolyzing when necessary. The specific examples and preparation methods of this type of water absorbing resin are disclosed in Japanese Kokai No. 52-25886, Japanese Kokoku No. 53-46199, Japanese Kokoku No. 53-46200, and Japanese Kokoku No. 55-21041.

Another example of water swellable/water absorbing resins includes hydrolyzed products of starch-acrylonitrile graft copolymers, hydrolyzed products of cellulose-acrylonitrile graft copolymers, crosslinked products of carboxymethylcellulose, partially hydrolyzed products of crosslinked polyacrylamide, crosslinked acrylic acid-acrylamide copolymers, crosslinked sulfonated polystyrenes, saponified products of vinyl ester-unsaturated carboxylic acid copolymers as disclosed in Japanese Kokai Nos. 52-14689 and 52-27455, crosslinked polyacrylic acid or salts thereof, crosslinked acrylic acid-acrylic ester copolymers, crosslinked isobutylene-maleic anhydride copolymers, crosslinked carboxylic modified polyvinyl alcohols, and self-crosslinking polyacrylic acid or salts thereof. The water absorbing resins described above may also be used in combination with one another.

In order to obtain the sufficient water retention characteristics., the water swellable/water absorbing resin preferably has a water absorption capacity of 50 g/g or more, most preferably 100–1,000 g/g based on the absorption of pure water.

The shapes of the water swellable/water absorbing resin are not particularly limited. Bead or particle-shaped materials and fibrous shaped materials are both preferably used in the present invention. Particle-shapes such as, for example, ground, granular, scaly, and pearly shaped beads are more preferable.

The particle size distribution of the water absorbing resin particles is not particularly limited. Preferably, about 95% or more by weight of the particles have a particle diameter of about 1 to about 1,000 microns. Most preferably, about 95% or more by weight of the particles have a particle diameter of about 50 to about 850 microns.

The fragrance and/or deodorant components used in the aqueous liquid in accordance with the present invention can be the substances which are commonly used as fragrance materials and deodorant materials. Alternatively, the component can be a fragrance with deodorant characteristics.

The fragrance component includes water soluble and water insoluble synthetic and natural fragrances as known in the art. In embodiments of the invention, the water soluble fragrance can be used as an aqueous solution. The non-water, oil soluble materials can be used as an aqueous emulsion containing water, and emulsifier, and optionally water-soluble solubilizers, co-solvents or other components necessary to produce the emulsion. The fragrance components also have odor masking effects to provide deodorant characteristics.

The deodorant component include the extracts of plants such as, rice, pine, Japanese cypress, bamboo grass, acidic or alkaline aqueous liquids, powdered activated carbon and the like as known in the art. These materials can be aqueous solutions diluted with water or a solution containing an organic solvent. Suitable organic solvents include, for example, polar solvents such as, lower alkyl alcohols such as ethanol, ketones such as, acetone and methylethylketone. Further, these materials may be used as aqueous emulsions as described above.

In preferred embodiments, the aqueous medium is an aqueous emulsion containing a fragrance or deodorant. Aqueous emulsions are generally preferred since a wide variety of oil-soluble fragrance and/or deodorant components can be used.

The packaged fragrance or deodorant material in accordance with the present invention can be produced by placing a water swellable/water absorbing resin in a packet or bag-like container having a water permeable portion. Preferably, the water absorbing resin is substantially dry and in a free flowing form for ease of handling. The container with the resin is immersed in an aqueous medium of the fragrance and/or deodorant components whereby the resin absorbs the medium and the fragrance or deodorant to form a gel in the container. The gel carries the fragrance and/or deodorant components in the container for slow release to the atmosphere through the porous portion of the container.

The methods for allowing the water absorbing resin in the container to absorb the aqueous solution are not particularly limited so long as they can effect the sufficient wet gel formation. In preferred embodiments the package is immersed into a bath of the aqueous medium for sufficient time for the resin to absorb the liquid. In further embodiments, the package is sprayed with the aqueous medium at a rate sufficient to enable the resin to absorb the aqueous medium and for a gel to form.

The amount of the aqueous medium containing the fragrance and/or deodorant components which is absorbed into the water swellable/water absorbing resin is dependent on the end use and is not particularly limited. When the amount of the aqueous medium introduced to container or the resin exceeds the maximum absorption capacity of the resin, the aqueous medium oozes out and leaks from the water absorbing resin during use, and the surface where the container contacts may become wet and dirty.

The amount of the aqueous medium absorbed into the water swellable/water absorbing resin can be adjusted, for example, by increasing or decreasing the immersion time when using immersion method. Alternatively, the spraying time can be increased or decreased to control the amount of the aqueous medium absorbed in the resin. The amount can also be adjusted by adjusting the volume of the package with respect to that of the water swellable/water absorbing resin contained in the container. The container and the resin can be immersed in the aqueous medium until the resin swells to completely fill the container. At that time, the container is removed from the aqueous medium.

Figure 3:
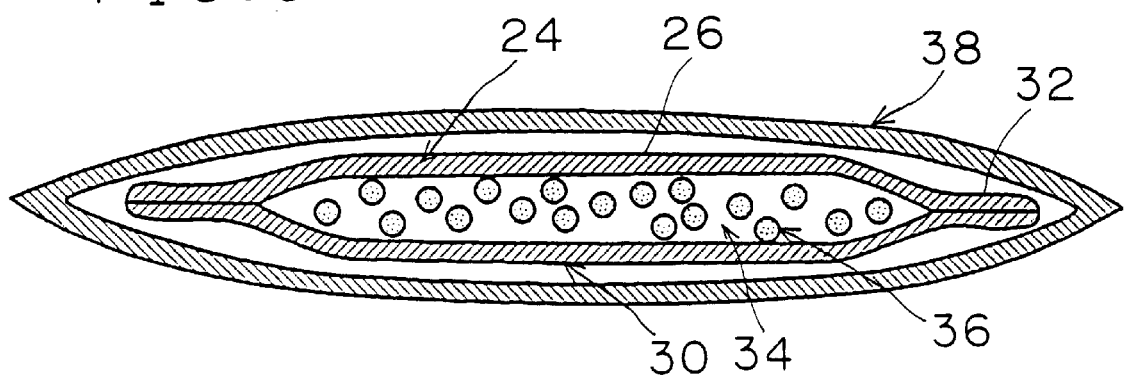
FIG. 3 is a cross sectional view showing another embodiment of a device fragrance or deodorant material in accordance with the present invention.

FIG. 3 is a cross section of another embodiment of a packet containing a fragrance or deodorant material in accordance with the present invention. Referring to FIG. 3, packet 24 includes a top layer 26 of a non-woven fabric, and bottom layer 30 of non-porous sheet of, for example, polyethylene. The edges 32 of packet 24 are bonded together around the perimeter to define cavity 34 which contains a gel 36 formed from a water absorbing resin. The gel 36 is produced in the same manner as in the embodiment of FIGS. 1 and 2. Packet 32 is enclosed in a non-porous, water impermeable envelope 38.

The packet 24 containing the gel 36 and fragrance or deodorant material shown in FIG. 3 is enclosed completely in envelope 38. Envelope 38 can be any suitable air impermeable film such as an ethylene-vinyl alcohol copolymer. The envelope 38 encloses packet 24 to prevent loss of the moisture and the volatile fragrance or deodorant during shipping and storage. Envelope 38 can have a frangible tear line (not shown) to assist in opening the envelope and removing the packet 24 for use by the consumer. In further embodiments, the packet 24 can be stored in other suitable airtight containers, such as airtight plastic or glass containers having a removable closure member. In this manner, the packet 24 can be removed from the container as needed. It is preferable that each packet be separately wrapped in a suitable non-water permeable material such as a plastic film and/or a metallic film. The wrapping materials can easily be removed by the user by cutting or tearing open the wrapping.

The envelope 38 is made from suitable materials including, for example, polyvinylidene chloride, ethylene-vinyl alcohol copolymer, and aluminum foil.

Preferably, the water and air impermeable envelope is a plastic film or a metallic film having an oxygen permeability constant of $1 \times 10^{10}$ cm3 (STP) * cm/cm2 * sec * cmHg or less in order to prevent the loss of the fragrance and/or deodorant components or other volatile components.

In the device containing the fragrance or deodorant materials in accordance with the present invention, the gelled water swellable/water absorbing resin having the aqueous medium absorbed therein eliminates the need to handle the gel during manufacture of the device. By placing the dry resin in the packet and then contacting the packet with the aqueous medium simplifies the manufacturing process device is made possible at lower costs.

During use, a user can readily use the device of the present invention by simply removing the device from the package. In addition, the device is small and compact so that it can be placed at any desired place such as on a corner of a room or an office, chest, closet, ashtray, trash can, shoe, shoe-closet, bathroom, or refrigerator. The device containing the fragrance or deodorant material of the present invention is more convenient than a conventional diffusing device, and exhibits excellent long-lasting fragrant or deodorant properties. Further, the material has no useless functions and no unnecessary materials or components, so that less waste is produced. Therefor, the device of the present invention is preferably from the view point of environmental protection and resource savings.

The following non-limiting example demonstrates one embodiment of the invention. However, it should be understood that the present invention is not limited thereto. All parts are based on weight unless otherwise indicated.

EXAMPLE 1

(1) Preparation of aqueous liquid containing fragrant component

A synthetic fragrance was used for a fragrance material. The following components were mixed in the given proportion, and sufficiently stirred to obtain a fragrance solution.

| | |
|---|---|
| terpene synthetic fragrance | 1 part |
| ethanol | 5 parts |
| Nonipole 120 (polyoxyethylenenonylphenyl ether nonionic surfactant by Sanyo Chemical Industries) | 3 parts |
| water | 91 parts |

(2) Preparation of a packet with water swellable/water absorbing resin

A polyester non-woven fabric and a polyethylene film each were cut into 5 cm×7 cm sections. 1 g of an acrylic water swellable/water absorbing resin was placed between the non-woven fabric and the polyethylene film, followed by heat sealing of the outer circumference to form a continuous heat sealed edge having a width of 5 mm. The acrylic water swellable/water absorbing resin had an average particle diameter of 20–50 microns, and a water absorption capability of 400 g/g.

(3) Preparation of a packet containing a fragrance material

The packet obtained in step (2) was immersed into the solution of the fragrance for 30 seconds. The packet was removed from the solution and the excess solution allowed to drain. The resin absorbed thirty times of its weight of the aqueous solution.

TEST EXAMPLE 1

The bagged fragrant material prepared in Example 1 was left in a room at 20–25° C. for 1 month. At the end of one month the packet of fragrance material still exhibited good fragrance release.

Various details of the invention may be changed without departing from the spirit or scope of the invention. Furthermore, the foregoing description of the embodiments according to the present invention is provided for the purpose of illustration only, and not for the purpose of limiting the invention as defined by the appended claims and their equivalents.

What is claimed is:

1. A device for releasing a fragrance, a deodorant material, or mixtures thereof to the atmosphere, wherein said device comprises a gel formed from a water absorbing, gel-forming resin and at least one of said fragrance, said deodorant material, or mixtures thereof, and a water insoluble container completely enclosing said gel, said container having a water and gas permeable portion for admitting an aqueous medium containing a fragrance, deodorant, or mixture thereof into said gel-forming resin, and wherein said device is produced by the process comprising the steps of enclosing a water absorbing gel-forming resin in a water insoluble container having at least one water permeable portion, and contacting said container with an aqueous medium containing at least one of said fragrance, said deodorant material, or mixtures thereof whereby essentially all of said aqueous medium penetrates said permeable portion and is absorbed by said resin to produce said gel containing said fragrance, said deodorant material, or mixtures thereof.

2. The device of claim 1, wherein said container is a packet of flexible material.

3. The device of claim 2, wherein said packet has a first side of a water insoluble, water permeable material.

4. The device of claim 3, wherein said first side is made from a non-woven fabric.

5. The device of claim 4, wherein said packet comprises a second side of a water insoluble, water impermeable material.

6. The device of claim 5, wherein said second side is bonded to said first side about a peripheral edge of said first and second sides by heat sealing.

7. The device of claim 1, wherein said aqueous medium is selected from the group consisting of aqueous solutions, aqueous emulsions and aqueous suspensions.

8. The device of claim 1, wherein said fragrance, said deodorant material, or mixtures thereof is an oil soluble fragrance or oil soluble deodorant material.

9. The device of claim 1, wherein said device is produced by a process further comprising the steps of enclosing said container in a substantially water and air impermeable material.

10. The device of claim 9, wherein said water and air impermeable material enclosing said container is a plastic film or a metal foil.

11. The device of claim 9, wherein said water and air impermeable material has an oxygen permeability constant of about $1 \times 10^{10}$ cm$^2$ (STP)·cm/cm$^2$·sec·cmHg or less.

12. A diffusing device for the sustained release of at least one a fragrance, a deodorant material, or mixtures thereof, comprising a flexible packet made from a substantially water insoluble material and having at least one water permeable portion for admitting an aqueous medium containing said fragrance, deodorant or mixture thereof into said packet and releasing said fragrance, deodorant or mixture thereof to the atmosphere, and a gelled water absorbing resin containing at least one of said fragrance, said deodorant material, or mixtures thereof, wherein said device is produced by a process comprising the steps of enclosing a substantially dry water absorbing gellable resin in a flexible packet, wherein said packet has a first side formed from a water insoluble and water permeable non-woven fabric and a second side made from a water insoluble, water impermeable sheet material, contacting said packet with an aqueous medium containing at least one of a fragrance, a deodorant material, or mixtures thereof whereby essentially all of said aqueous medium penetrates said water permeable layer and is absorbed by said resin to form a gel containing said fragrance, said deodorant material, or mixtures thereof.

13. The device of claim 12, wherein said non-woven fabric and sheet material are heat sealed together around a perimeter of said packet.

14. The device of claim 12, wherein said aqueous medium is selected from the group consisting of aqueous solutions, aqueous emulsions, and aqueous suspensions.

15. A process for producing a diffusing device for the sustained release of a fragrance, a deodorant material, or mixtures thereof, said process comprising the steps of forming a substantially closed container containing a substantially dry water absorbing, gellable resin, wherein said container is substantially water insoluble and includes at least one water permeable portion for enabling an aqueous medium containing a fragrance, deodorant, or mixture thereof to pass through while retaining said resin in said container, and contacting said container with an aqueous medium containing at least one of a fragrance, a deodorant material, or mixtures thereof whereby essentially all said aqueous medium passes through said water permeable portion and contacts said resin to form a gelled resin containing said at least one of said fragrance, said deodorant material, or mixtures thereof.

16. The process of claim 15 wherein said container is a flexible packet having at least one side made of a non-woven fabric.

17. The process of claim 15, wherein said container is a flexible packet having a first layer made of a non-woven fabric and a second layer made of a water impermeable.

18. The process of claim 17, wherein said first and second layers are heat sealed together about peripheral edges thereof to enclose said resin.

19. The process of claim 15, wherein said aqueous medium is selected from the group consisting of aqueous solutions, aqueous emulsions and aqueous suspensions.

20. The process of claim 15, wherein said container is immersed in said aqueous medium for sufficient time for said resin to absorb said aqueous medium.

21. The process of claim 15, wherein said container is sprayed with said aqueous medium whereby said resin is contacted with said aqueous medium.

22. The device of claim 1, wherein said resin has a water absorption capacity of about 50 g/g or more.

23. The device of claim 1, wherein said resin has a water absorption capacity of about 100 g/g to about 1,000 g/g.

24. The device of claim 1, wherein said gel-forming resin is a particulate.

25. The process of claim 15, wherein said resin has a water absorption capacity of about 50 g/g or more.

26. The process of claim 15, wherein said resin has a water absorption capacity of about 100 g/g to about 1,000 g/g.

27. The process of claim 15, wherein said aqueous medium contains an effective amount of said fragrance or deodorant to enable said device to release said fragrance or deodorant to the atmosphere.

28. The process of claim 27, wherein said aqueous medium is about 1% by weight of said fragrance or deodorant.

* * * * *